United States Patent [19]
Linhart

[11] Patent Number: 5,671,266
[45] Date of Patent: Sep. 23, 1997

[54] X-RAY EXAMINATION APPARATUS

[75] Inventor: Claus Linhart, Hamburg, Germany

[73] Assignee: U.S. Philips Corporation, New York, N.Y.

[21] Appl. No.: 529,183

[22] Filed: Sep. 15, 1995

[30] Foreign Application Priority Data

Sep. 16, 1994 [DE] Germany ............... 44 33 036.7

[51] Int. Cl.⁶ .................................................. G03B 42/04
[52] U.S. Cl. ........................ 378/175; 378/177; 378/195
[58] Field of Search ........................ 378/167, 172–175,
378/177, 181, 190, 195, 209, 210; 318/466, 467, 626

[56] References Cited

U.S. PATENT DOCUMENTS

| | | |
|---|---|---|
| 4,587,471 | 5/1986 | Barthelmes et al. ............ 318/628 |
| 4,829,844 | 5/1989 | Boomgaarden et al. .............. 74/470 |
| 5,050,202 | 9/1991 | Yanome .............................. 378/167 |

FOREIGN PATENT DOCUMENTS

| | | | |
|---|---|---|---|
| 0380076 | 8/1990 | European Pat. Off. . | |
| 2460441 | 6/1976 | Germany . | |
| 2739934 | 3/1979 | Germany | ................. A61B 6/00 |
| 3236116 | 3/1984 | Germany . | |

*Primary Examiner*—Don Wong
*Attorney, Agent, or Firm*—Jack D. Slobod

[57] ABSTRACT

An X-ray examination apparatus (1), includes a patient table (2) and an X-ray spotfilm device (4) which is reciprocatable in at least two spatial directions relative to the patient table (2), as well as sensors (8a, 8b, 8c, 8d) which are integrated in an operating grip (10) of the X-ray spotfilm device (4) and which serve to activate at least one servomotor (5,7) for the X-ray spotfilm device. In order to make a single operating grip (10) suffice for sliding the X-ray spotfilm device in at least four feasible of movement, the sensors are arranged in such a manner that when the operating grip is exposed to a force in an arbitrary one of the at least four feasible directions of movement, each time a different group (8a, 8b; 8c, 8d; 8a, 8c; 8b, 8d) of sensors (8a, 8b, 8c, 8d) is activated.

12 Claims, 3 Drawing Sheets

X-RAY EXAMINATION APPARATUS

BACKGROUND OF THE INVENTION

1. Field of the Invention

The invention relates to an X-ray examination apparatus, including a patient table and an X-ray spotfilm device which is reciprocatable in at least one spatial direction relative to the patient table, as well as sensors which can be activated by an operating grip of the X-ray spotfilm device so as to activate at least one servomotor of the X-ray spotfilm device.

2. Description of the Related Art

In X-ray examination apparatus, notably in directly controlled X-ray fluoroscopy apparatus, the radiologist moves the X-ray spotfilm device across a patient, arranged so as to be immobile on the patient table, in order to detect anomalies quickly and hence without exposing the patient to a high radiation dose. Because the X-ray spotfilm device comprises inter alia an X-ray source, an image detector and an image intensifier and hence has a comparatively large inertia mass, servomotors are used to intensify the forces exerted by the radiologist on the operating grip of the X-ray spotfilm device to so that the spotfilm device can be easily displaced by the radiologist exerting large forces. The displacement of the X-ray spotfilm device generally takes place in the longitudinal direction of the patient table and perpendicularly thereto in the compression direction towards and away from the patient.

The servomotors should operate as inconspicuously as possible, i.e. the force should be supplemented as smoothly as possible in the desired spatial direction in conformity with the intensity of the forces induced in the X-ray spotfilm device by the radiologist. This purpose is served by the sensors which are activated by the operating grip and which measure the force exerted on a gripping surface of the operating grip by the radiologist, said sensors ensuring that a supplementary force of the desired intensity is delivered by the servomotor. In order to facilitate operation, the intensification should be essentially proportional to the force applied in the relevant spatial direction. Such intensification corresponds to natural patterns of movement, for example the application of a large force for fast approach of a desired area of the body or the application of a small force for accurate adjustment of the spotfilm device, so that the radiologist subjectively experiences an apparatus of very small mass which follows the forces he exerts.

DE-OS 27 39 934 discloses an X-ray examination apparatus of the kind in which the operating grip comprises a sleeve which can reciprocate in its longitudinal direction between two abutment surfaces, sensors being provided in the form of discs of a pressure-dependent resistive material arranged between a respective end face of the sleeve and one of the abutment surfaces, said discs forming part of a bridge circuit associated with the control circuit of the servomotor. When the disc is loaded by a compressive force, the bridge circuit is decompensated and the voltage then occurring in its diagonals is amplified by an operational amplifier and applied to a differential amplifier whose output voltage is extracted so as to drive the servomotor via a thyristor assembly. However, in the known X-ray spotfilm device only the forces applied in the longitudinal direction of the operating grip can be intensified, so that an X-ray spotfilm device moveable to and fro in each of spatial two different directions requires two of such operating grips; this leads to substantially complicated handling.

SUMMARY OF THE INVENTION

Therefore, if is an object of the invention to improve an X-ray examination apparatus of the kind set forth in such a manner that it can be moved to and fro in a force-intensified manner along each of two different spatial directions by engaging a single operating grip.

This object is achieved in accordance with the invention in that the X-ray spotfilm device can be moved to and fro in each of at least two different spatial directions by means of a single operating grip, and that the sensors are arranged relative to the operating grip in such a manner that when a force is applied to the operating grip in an arbitrary one of the at least four feasible directions of movement, each time a different group of at least two of the sensors is activated.

In a further embodiment of the invention, the X-ray spotfilm device can be reciprocated in a third spatial direction which preferably extends perpendicularly to said mutually perpendicular spatial directions, the sensors being arranged in such a manner that when a force is applied in a direction which corresponds to an arbitrary one of the six feasible directions of movement, each time a given group of at least two sensors is activated, which group always differs from the groups which are activated when the direction of the force is different and corresponds to one of the five other feasible directions of movement. Alternatively, or additionally, a rotary or pivotal movement of the X-ray spotfilm device about a pivot axis may be envisaged, in which case the sensors are again arranged in such a manner that different groups of sensors are activated in dependence on the direction of an applied force. When a force is applied with a force vector combined from two or more of the spatial or rotary directions, several sensor groups which are preferably formed as sensor pairs are activated, their signals then being used to drive a servomotor operating in the corresponding direction of movement.

A preferred embodiment of the invention is characterized in that it comprises at least one deformable force transmission member which is arranged between the operating grip and each sensor and which is made of an incompressible material which preferably has elastic properties. The material between the sensor and the operating grip serves as a pressure transmission medium for converting a force applied to the gripping surface by an operator into an omnidirectional pressure in one or more of the force transmission members, said pressure then acting on an active surface of the sensor, effectively constructed as a pressure or force sensor with a large dynamic range and low space requirements, preferably as a foil pressure sensor, in which it produces a force proportional to the relevant pressure, which force itself causes a resistance variation in the sensor. The incompressible material preferably has gum elastic properties, so that it returns to its original position when the operating grip is released. A preferably rigid connection between the force transmission member and the sensor can be realized, for example by gluing the sensor onto the force transmission member or effectively by embedding the sensor, connected to the supporting member of the operating grip, in the force transmission member. Even though the sensors and the force transmission members may also be arranged outside the operating grip, they are preferably integrated in the grip.

The operating grip may be conceived so that exclusively forces directed parallel to the feasible movement directions can be applied to the force transmission members, whereas forces in other spatial directions are taken up, for example, directly by the X-ray spotfilm device.

In a further preferred embodiment of the invention, the individual sensor signals are applied to a processing circuit which supplies the servomotors with drive energy only if all sensor signals of a respective group are at least approximately of the same order of magnitude. In the case of failure of a sensor, the X-ray examination apparatus can thus be switched off to enhance its safety.

The magnitude of the sensor signals is determined by the magnitude of the force application surfaces via which the operating grip acts on the force transmission members. A large force application surface in a movement direction in which the X-ray spotfilm device has a comparatively small inertia mass and a small force application surface in a movement direction in which the X-ray spotfilm device has a comparatively large inertia mass lead to different pressures in the force transmission member in response to application of equally large forces and hence to different force intensification by the servomotors with the same characteristic of the force sensors; as a result the radiologist will actually not experience the unequal inertia masses during displacement of the X-ray spotfilm device. Because the inertia masses are known already at the conception of the X-ray examination apparatus, they can be taken into account for the proportioning of the force application surfaces so that a downstream amplifier may then become superfluous.

Unequal force intensification can also be realized in the described manner when, for example with the same applied force the X-ray spotfilm device is to be accelerated more in one spatial direction, for example the longitudinal direction of the patient table, than in another spatial direction, for example the compression direction.

BRIEF DESCRIPTION OF THE DRAWING

The invention will be described in detail hereinafter with reference to the accompanying drawing. Therein.

DETAILED DESCRIPTION OF THE PREFERRED EMBODIMENTS

Figure 1:
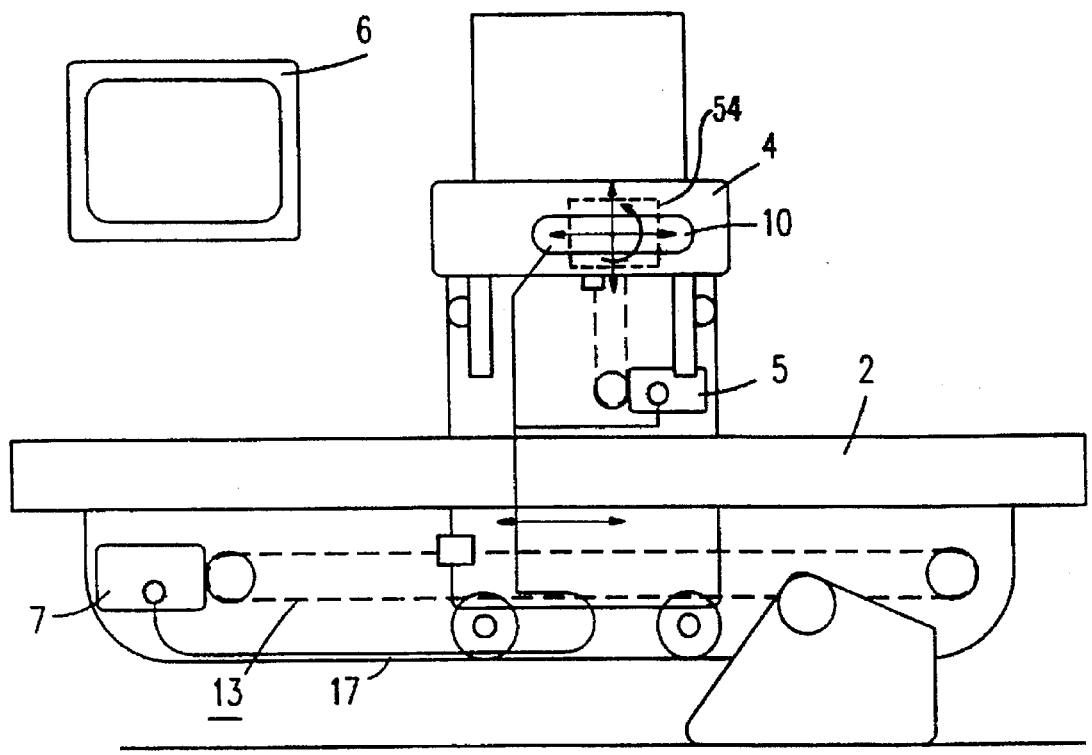
FIG. 1 is a side elevation of an X-ray examination apparatus in accordance with the invention.

The X-ray examination apparatus 1 which is diagrammatically shown in FIG. 1 comprises essentially a patient table 2 which can be pivoted from a horizontal to a vertical position by means of a motor, and also an X-ray spotfilm device 4 which can be displaced in the longitudinal direction of the patient table 2 and in the compression direction (perpendicularly to the patient table 2). The X-ray spotfilm device 4 comprises inter alia an image detector as well as an image intensifier for converting and displaying an X-ray image received from the image detector on a monitor 6; the spotfilm device is coupled to an X-ray source which can be moved underneath the patient table, and therefore, has a comparatively large inertia mass. In order to facilitate the reciprocation of the X-ray spotfilm device 4 in the longitudinal direction of the patient table 2 and in the compression direction, there are provided servomotors 5, 7 which deliver the major part of the force required to move the X-ray spotfilm device 4, so that latter can be readily displaced by the radiologist (FIG. 1).

Figure 2:
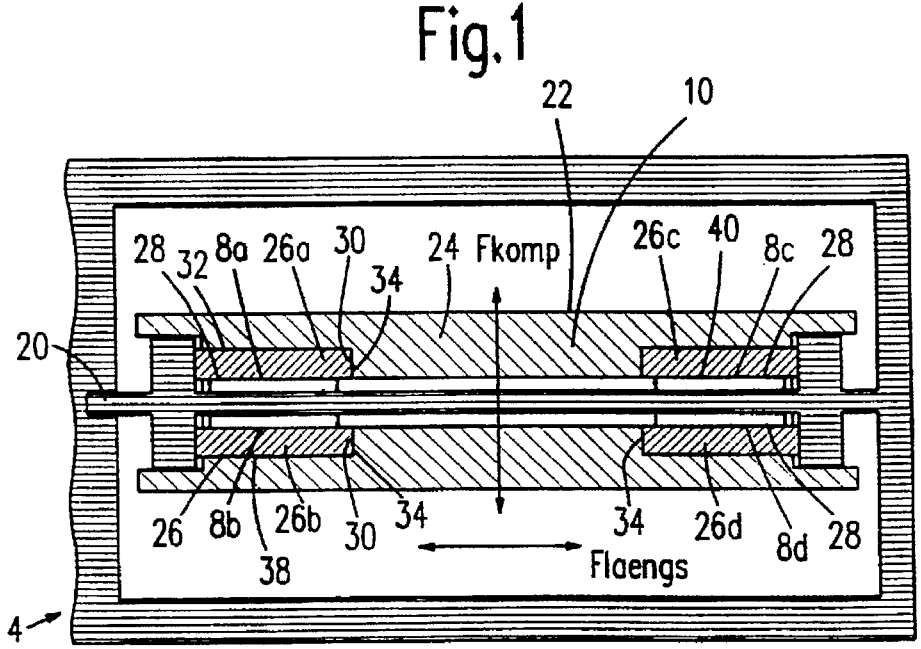
FIG. 2 is a longitudinal sectional view of the operating grip of the X-ray examination apparatus shown in FIG. 1.
Figure 3:
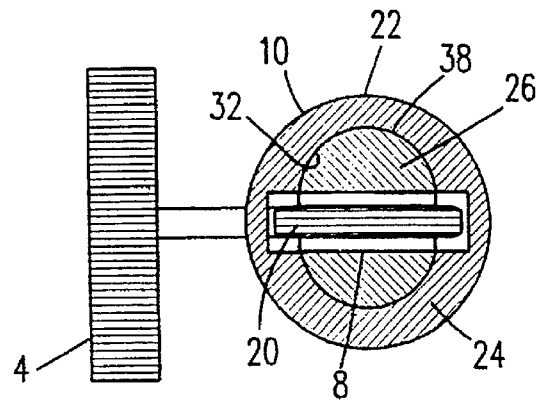
FIG. 3 is a cross-sectional view of the operating grip.

The servomotors 5, 7 are appropriately driven by means of four sensors 8a, 8b, 8c, 8d which are constructed as foil pressure sensors, integrated in an operating grip 10 of the X-ray spotfilm device 4 and connected to the servomotors 5, 7 via control leads 17 (see FIGS. 2 and 3). They serve to detect a force applied to the operating grip 10 by the radiologist in one of the four feasible movement directions of the X-ray spotfilm devices 4 (i.e. in opposite directions in the longitudinal direction of the patient table 2 as well as in the compression direction); this force is detected in the form of a resistance variation in each time two (8a, 8b; 8e, 8d; 8a, 8e; 8b, 8d) of the four foil pressure sensors 8a, 8b, 8c, 8d. As will be described in detail hereinafter, the resistance of the foil pressure sensors 8a, 8b, 8c, 8d used decreases essentially in proportion to a pressure acting on their active surface to such an extent that the resistance variation can be used directly as a control variable, without further amplification, for the servomotors 5, 7.

Figure 6:
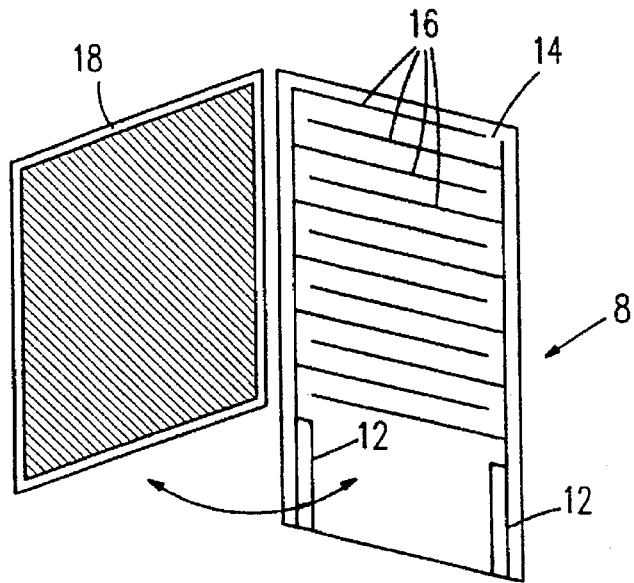
FIG. 6 is an exploded view of a foil pressure sensor for an operating grip of an X-ray examination apparatus.

The foil pressure sensors 8a, 8b, 8c, 8d essentially consist of two electrodes 12 which are constructed in the form of a comb and which are arranged on a polymer film 14 in such a manner (FIG. 6) that their mutually parallel conductor segments 16 mesh, the distance between and the width of the meshing conductor segments 16 amounting to approximately 0.4 mm. On the upper side of the electrodes 12 which is remote from the polymer film 14 there is deposited a further film 18 which consists of a semiconductor polymer (shown in the folded-away state in FIG. 6) and which covers the electrodes 12 and the polymer film 14 in such a manner that the conductor segments 16 are connected in parallel by the film 18 in the form of a semiconductor. When one of the broadside faces of such a foil pressure sensor 8a, 8b, 8c, 8d is uniformly exposed to pressure, its resistance decreases essentially in proportion to the value of the pressure exerted, the order of magnitude of the resistance decrease corresponding essentially to that of the pressure increase.

The operating grip 10 consists essentially of a supporting element 20 which is rigidly connected to the X-ray spotfilm device 4, a grip section 24 which is provided with a gripping surface 22, the four foil pressure sensors 8a, 8b, 8e, 8d, and four deformable force transmission members 26, each of which is arranged between a respective foil pressure sensor 8a, 8b, 8c, 8d and the grip section 24, said force transmission members consisting of an incompressible material having gum elastic properties. The four foil pressure sensors 8 are arranged pair-wise on opposite end faces of the supporting element 20 and on opposite sides of the supporting element 20 in such a manner that their broadside faces extend parallel to the longitudinal direction of the operating grip 10 and their active surfaces 28 are always oriented in the compression direction towards one of the force transmission members 26. The oil pressure sensors 8a, 8b, 8e, 8d are rigidly connected to the supporting element 20 on the one side and to the associated force transmission member 26 on the other side, the joint being realized, for example by gluing the foil pressure sensors 8a, 8b, 8c, 8d to the supporting element 20, followed by gluing the force transmission members 26 to the foil pressure sensors 8a, 8b, 8c, 8d, or by embedding the foil pressure sensors 8a, 8b, 8e, 8d glued to the supporting element into the force transmission member 26.

Accompanied by a slight deformation of each time two of the force transmission members 26, the grip section 24 can be moved to and fro, relative to the supporting element 20, in a restricted fashion, in the longitudinal direction of the supporting element 20 (corresponding to the longitudinal direction of the patient table 2) as well as in the direction transversely thereof (corresponding to the compression direction), and engages each of the force transmission members 26 by way of two surfaces 30, 32 which act as force application surfaces. Whereas the force application faces 30 engaging opposite end faces 34 of the force transmission members 26 extend perpendicularly to the longitudinal direction of the operating grip 10, and hence perpendicularly to the longitudinal direction of the patient table 2, the force application faces 32 engaging a semi-cylindrical circumferential surface 38 of the force transmission members 26 have a semi-cylindrical shape which corresponds to the shape of the circumferential surface 38.

The force transmission members 26, being made of a soft elastomer material, are integrated in the operating grip 10 in such a manner that they cannot yield when the operating grip 10 is exposed to a force in the longitudinal direction of the patient table 2 or in the compression direction, i.e. they are confined on all sides by the force application faces 30, 32, by one or more abutment faces of the supporting element 20 which face the force application faces 30, 32, as well as by the foil pressure sensors 8a, 8b, 8c, 8d. The force transmission members 26, therefore, behave as an incompressible liquid, which means that a force acting on its boundary faces 34, 38 is converted into a pressure in the force transmission member 26 in conformity with the ratio of the force to the surface component perpendicular to the force direction, which pressure propagates omnidirectionally throughout the force transmission member 26 and acts on all boundary faces, i.e. also on a boundary face 40 of the force transmission member 26 which engages the active surface 28 of the foil pressure sensor 8a, 8b, 8c, 8d.

Because this boundary face 40 serves to transmit the pressure to the foil pressure sensor 8a, 8b, 8c, 8d in the case of forces in the longitudinal direction of the operating grip 10 ($F_{laengs}$) as well as for forces in the compression direction ($F_{komp}$), the intensification Of the forces is dependent exclusively on the magnitude of the force application faces 30, 32 or on the magnitude of their projections in a direction perpendicular to the direction of $F_{laengs}$ or $F_{komp}$. Thus, when the force application faces 30 and 32 are of different dimensions, equally large forces exerted on the grip section 24 in the longitudinal direction and in the compression direction result in different pressures in the force transmission members 26 exposed to the force, and hence to unequal voltage signals in the foil pressure sensor 8, thus causing different force intensifications by the servomotor.

Thus, unequal sensitivities of the device, for example, caused by the fact that the inertia masses of the X-ray spotfilm device 4 to be displaced in the longitudinal direction of the patient table 2 or in the compression direction are unequal, can be compensated or corrected by appropriate proportioning of the force application faces 30, 32 or their projections in a direction perpendicular to the relevant force component in the movement directions of the X-ray spot film device 4. In comparison with mathematical correction or correction by unequal amplification of the signals, such a correction has the advantage of being firmer, less susceptible to disturbances and easy to adjust.

Figure 4:
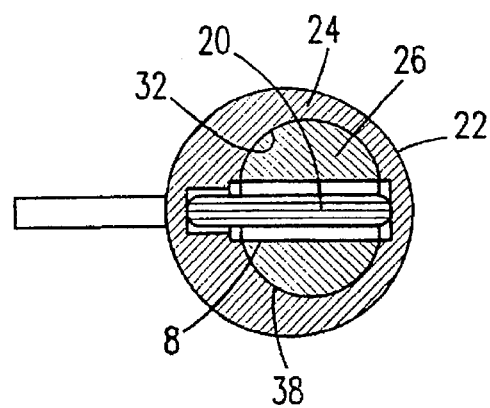
FIG. 4 is a cross-sectional view of an alternative embodiment of the operating grip.

In order to illustrate this, in the embodiment shown in the FIGS. 2 and 3 the force application face 30 for $F_{laengs}$ corresponds approximately to the boundary face 40 of the force transmission member 26 which engages the active face 28 of the foil pressure sensor 8a, 8b, 8c, 8d, whereas the respective force application faces 32 for $F_{komp}$ are substantially larger, so that when the absolute values of $F_{laengs}$ and $F_{komp}$ correspond, the pressure-induced resistance decrease by $F_{laengs}$ is substantially greater. In addition to the compensation of unequal inertia masses, the one-sided arrangement of the operating grip 10 on the X-ray spotfilm device 4 and the resultant torque can thus also be compensated. This can also be achieved by arranging the foil pressure sensors 8a, 8b, 8c, 8d and the force transmission members 26 in the operating grip 10 so as to be displaced perpendicularly to $F_{laengs}$ and $F_{komp}$, and by a one-sided clamping of the supporting element 20 in the grip section 24 as shown in FIG. 4.

Figure 7:
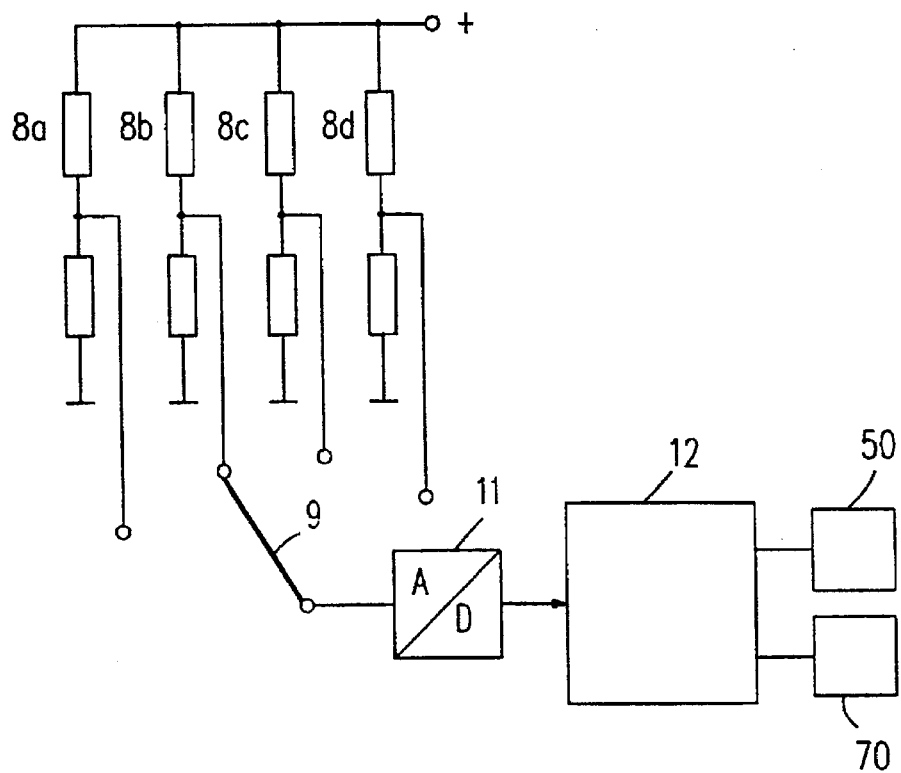
FIG. 7 shows a load/resistance characteristic of a foil pressure sensor for an operating grip of an X-ray examination apparatus.

Appropriate intensification of $F_{laengs}$ and $F_{komp}$ during displacement of the X-ray spotfilm device 4 in an arbitrary one of the four possible movement directions gives the radiologist the sensation of moving only a very small inertia mass with natural movement patterns because of the essentially proportional intensification, due to the approximately linear characteristic of the foil pressure sensors 8a, 8b, 8c, 8d shown in FIG. 7, since large forces are intensified proportionally more than small forces.

In a direction perpendicular to the longitudinal direction of the patient table 2 and to the compression direction, the grip section 24 is journalled in such a manner that it cannot be moved relative to the supporting element 20, i.e. it engages the supporting element 20 directly without intermediate force transmission members 26, so that forces applied to the grip section 24 in this direction do not increase the pressure in one of the force transmission members 26 and hence do not cause activation of the servomotors 5, 7.

When the operating grip 10 is exposed to a force in one of the two opposite directions of $F_{laengs}$ and $F_{komp}$, this force is always applied to two force transmission members 26. In the case of a force $F_{laengs}$ to the left in FIG. 2, for example the two force transmission members 26a and 26b are pressure loaded, and hence the resistance of the two foil pressure sensors 8a and 8b is changed whereas in the case of a force $F_{laengs}$ to the right in FIG. 2 the two force transmission members 26c and 26d are pressure loaded and the resistance of the foil pressure sensors 8c and 8d is changed. Analogously, in the case of a force $F_{komp}$ in the downwards direction in FIG. 2, the two force transmission members 26a and 26c are pressure loaded and the resistance of the foil pressure sensors 8a and 8c is changed whereas a force $F_{komp}$ in the upwards direction in FIG. 2 exposes the two force transmission members 26b and 26d to a pressure load, thus changing the resistance of the two foil pressure sensors 8b and 8d. The force application faces 30, 30 or 32, 32 of the force transmission members 26a, 26b; 26c, 26d or 26a, 26c; 26b, 26d, each time loaded together, are always equal, so that the pressure increase in the force transmission members 26a, 26b; 26c, 26d; 26a, 26c or 26b, 26d and the associated resistance decrease in the relevant associated two foil pressure sensors 8a, 8b; 8e, 8d; 8a, 8c or 8b, 8d are also equal.

FIG. 7 shows a circuit suitable for converting the resistance variations into control signals for the servomotors. Therein, the sensors 8a. . . 8d form part of a respective voltage divider which is connected to a direct voltage. The voltages on the taps, being higher as the pressure on the associated sensor is greater, are applied to a microcontroller 12 via a multiplexer 9 and an A/D converter 11. The microcontroller controls the servomotors 5 and 7 in respect of speed and direction of rotation via controllers 50 and 70.

The microcontroller 12 is programmed so that it determines whether two voltages are present which are approximately equal and different from zero and also with which sensors these voltages are associated. For example, in the case of two voltages from the sensors 8c and 8c, the servomotor 7 is activated via the controller 70 in such a manner that the spotfilm device is displaced to the right in the longitudinal direction; if the voltages originate from two other sensors, displacement occurs in another direction. The speed is then dependent on the value of the voltages.

If two strongly deviating voltages are detected, or only one voltage which exceeds a threshold, a defect or failure of a sensor is hinted. Injury to a patient or the radiologist due to unintentional motion of the X-ray spotfilm device is then automatically prevented by deactivation of the servomotors 5a, 5b, 7.

Figure 5:
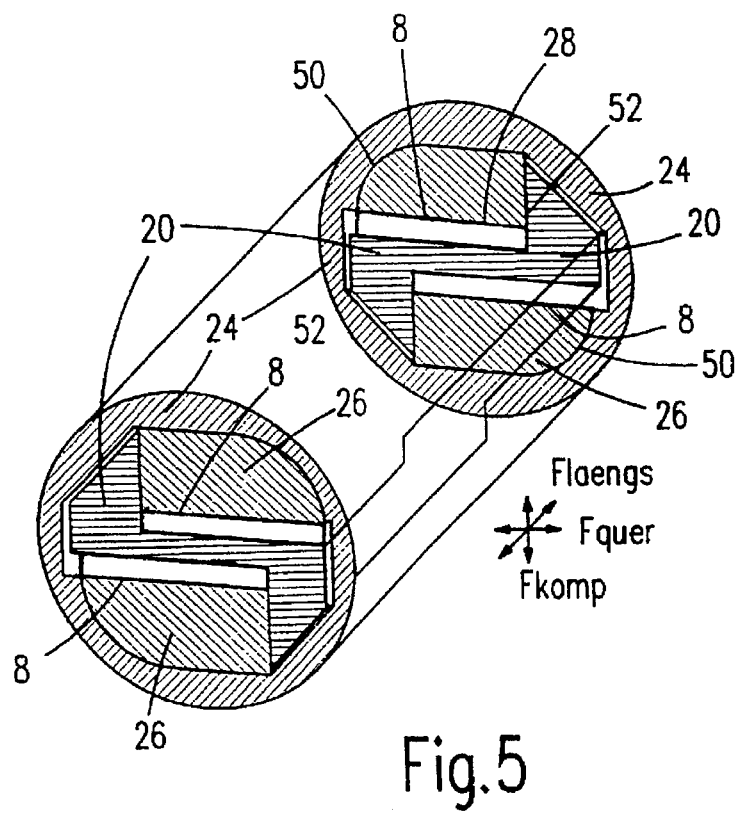
FIG. 5 shows two perspective cross-sectional views of a further alternative embodiment of the operating grip.

The operating grip 10 shown in FIG. 5 can be used in conjunction with an X-ray spotfilm device 4 which is displaceable in the direction of $F_{laengs}$ and $F_{komp}$ as well as in a direction perpendicular thereto. As a result of an asymmetrical construction of the supporting element 20 and the force transmission member 26, a further force application face 50 is formed on each force transmission member 26 therein, which further force application face is situated opposite an abutment face 52 of the supporting element 20 so that when a force $F_{quer}$ which is directed perpendicularly to $F_{laengs}$ and $F_{komp}$ is applied to the grip section 24, a pressure which causes a resistance variation of the foil pressure sensor 8a, 8b, 8c, 8d is produced in each time two of the force transmission members 26.

Analogously, the supporting element 20, the grip section 24 and the force transmission members 26 can also be constructed and arranged in the operating grip 10, together with four foil pressure sensors 8a, 8b, 8c, 8d, in such a manner that instead of a motion perpendicular to $F_{laengs}$ and $F_{komp}$, a pivotal motion about an axis of rotation perpendicular to $F_{laengs}$ and $F_{komp}$ is possible, and hence a corresponding force intensification in the direction of rotation by way of a further servomotor 54 (see FIG. 1).

I claim:

1. An X-ray examination apparatus, comprising a patient table and an X-ray spotfilm device which is moveable relative to the patient table to and fro in each of first and second spatial directions, corresponding to at least four feasible directions of movement, as well as sensors which can be activated by an operating grip of the X-ray spotfilm device in order to activate one or more servomotors of the X-ray spotfilm device, wherein the sensors are arranged relative to the operating grip in such a manner that when a force is applied to the operating grip in different ones of the at least four feasible directions of movement, a different combination of at least two of the sensors is activated for each of the at least four feasible directions of movement.

2. An X-ray examination apparatus as claimed in claim 1, wherein individual signals from one of the combinations of at least two of the sensors are applied to a processing circuit which supplies the servomotors with drive energy only if all of said individual signals from said one of the combinations of at least two of the sensors are at least approximately of the same order of magnitude.

3. An X-ray examination apparatus as claimed in claim 1, wherein it comprises of one or more deformable force transmission members which are arranged between the operating grip and associated ones of the sensors, said force transmission members being made of an incompressible material having elastic properties.

4. An X-ray examination apparatus as claimed in claim 3, wherein the associated sensors and force transmission members are arranged between a supporting element which is rigidly connected to the X-ray spotfilm device and a grip section of the operating grip which is provided with a gripping surface.

5. An X-ray examination apparatus as claimed in claim 4, wherein the force transmission members comprise force application faces for the grip section which extend perpendicularly to the feasible directions of movement of the associated sensors.

6. An X-ray examination apparatus as claimed in claim 4, wherein application of a force, or force components, to the operating grip in a direction perpendicular to the feasible directions of movement of the X-ray spotfilm device does not cause a pressure increase in one of the force transmission members.

7. An X-ray examination apparatus as claimed in claim 4, wherein each different combination of sensors is arranged pair-wise at opposite ends of the operating grip and at opposite sides of the supporting element.

8. An X-ray examination apparatus, comprising a patient table and an X-ray spotfilm device which is moveable relative to the patient table in each of first, second, and third spatial directions, corresponding to six feasible directions of movement, as well as sensors which can be activated by an operating grip of the X-ray spotfilm device in order to activate at least one servomotor of the X-ray spotfilm device, wherein the sensors are arranged relative to the operating grip in such a manner that when a force is applied to the operating grip in different ones of the six feasible directions of movement, a different combination of at least two of the sensors is activated for each of the at six feasible directions of movement.

9. An X-ray examination apparatus as claimed in claim 8, wherein individual signals from one of the combinations of at least two of the sensors are applied to a processing circuit which supplies the servomotors with drive energy only if all of said individual signals from said one of the combinations of at least two of the sensors are at least approximately of the same order of magnitude.

10. An X-ray examination apparatus as claimed in claim 8, wherein said first and second spatial directions of movement are linear and said third direction of movement is rotational.

11. An X-ray examination apparatus as claimed in claim 10, wherein individual signals from one of the combinations of at least two of the sensors are applied to a processing circuit which supplies the servomotors with drive energy only if all of said individual signals from said one of the combinations of at least two of the sensors are at least approximately of the same order of magnitude.

12. An X-ray examination apparatus comprising a patient table and an X-ray spotfilm device which is moveable relative to the patient table to and fro in each of first and second spatial directions, corresponding to at least four feasible directions of movement, as well as sensors which can be activated by an operating grip of the X-ray spotfilm device in order to activate one or more servomotors of the X-ray spotfilm device, wherein the sensors are arranged relative to the operating grip in such a manner that when a force is applied to the operating grip in different ones of the at least four feasible directions of movement, a different combination of at least two of the sensors is activated for each of the at least four feasible directions of movement, and wherein the sensors are constructed as foil pressure sensors.

* * * * *